(12) United States Patent
Igarashi

(10) Patent No.: US 8,447,388 B2
(45) Date of Patent: May 21, 2013

(54) APPARATUS AND METHOD FOR BIOLOGICAL OBSERVATION USING SOUND WAVES AND LIGHT

(75) Inventor: Makoto Igarashi, Tokyo (JP)

(73) Assignee: Olympus Medical Systems Corporation, Tokyo (JP)

( * ) Notice: Subject to any disclaimer, the term of this patent is extended or adjusted under 35 U.S.C. 154(b) by 404 days.

(21) Appl. No.: 12/391,536

(22) Filed: Feb. 24, 2009

(65) Prior Publication Data

US 2009/0221911 A1 Sep. 3, 2009

(30) Foreign Application Priority Data

Feb. 25, 2008 (JP) .................................. 2008-043193

(51) Int. Cl.
*A61B 6/00* (2006.01)

(52) U.S. Cl.
USPC ............ 600/473; 600/407; 600/437; 600/476

(58) Field of Classification Search
USPC ................. 600/427, 407, 437, 473, 476, 310, 600/443, 456
See application file for complete search history.

(56) References Cited

U.S. PATENT DOCUMENTS

| | | | |
|---|---|---|---|
| 2005/0085725 A1* | 4/2005 | Nagar et al. | 600/437 |
| 2006/0173292 A1* | 8/2006 | Baba et al. | 600/425 |
| 2007/0187632 A1* | 8/2007 | Igarashi | 250/559.36 |
| 2007/0282203 A1* | 12/2007 | Baba et al. | 600/453 |

FOREIGN PATENT DOCUMENTS

| | | |
|---|---|---|
| EP | 1 810 610 | 7/2007 |
| JP | 2000-88743 | 3/2000 |
| JP | 2000-197635 | 7/2000 |
| JP | 2007-504883 | 3/2007 |
| WO | WO 2005/025399 | 3/2005 |

* cited by examiner

*Primary Examiner* — James Kish
*Assistant Examiner* — Michael N Fisher
(74) *Attorney, Agent, or Firm* — Scully, Scott, Murphy & Presser, P.C.

(57) ABSTRACT

A biological observation apparatus according to the present application includes a sound wave radiating unit that radiates a sound wave into an object to be examined in living tissue, a light radiating unit that radiates light into the object, a light interfering unit that makes the light radiated from the light radiating unit interfere with light reflected from an area where the sound wave reaches and radiates interference light, a light detector that detects the interference light radiated from the light interfering unit and outputs an interference signal corresponding to the interference light, and a calculation unit that calculates the amount of frequency modulation of the radiated light based on the interference signal outputted from the light detector and calculates a difference value between the two adjacent amounts of frequency modulation in sequence.

12 Claims, 7 Drawing Sheets

APPARATUS AND METHOD FOR BIOLOGICAL OBSERVATION USING SOUND WAVES AND LIGHT

CROSS REFERENCE TO RELATED APPLICATION

The present application relates to and incorporates by reference Japanese Patent application No. 2008-043193 filed on Feb. 25, 2008.

BACKGROUND OF THE INVENTION

1. The Field of the Invention

The present invention relates to a biological observation apparatus and method and, more particularly, to a biological observation apparatus and method which use a sound wave and light to obtain information indicative of internal states of living tissue.

2. Related Art

In recent years, as optical tomographic imaging for a living body, there have been known optical CT (computed tomography), optical coherence tomography (hereinafter, referred to as "OCT"), and photoacoustic tomography.

The optical CT utilizes near-infrared light of a wavelength ranging from 700 nm to 1200 nm, which is comparatively weakly influenced by scattering in a living body. Therefore, the optical CT enables to obtain tomograms of deep parts in a living body, such as up to several centimeters under a mucous membrane.

The OCT, which utilizes interference, can obtain tomographic images of a living body up to a depth of about 2 mm with high resolution (several μm to several tens of μm) in a short time. The OCT has already been put into practice in diagnosing retinopathy in the ophthalmic field. Therefore, OCT has attracted very keen interest in the medical world.

Although the optical CT can obtain information on a deep part of a living body, its spatial resolution is as low as several millimeters. In contrast, it is difficult for the OCT to perform observation at a depth of about 2 mm or more under a mucous membrane and to provide a good quality image of tumor tissue, such as a cancer. This is because the optical coherence is greatly disturbed by the influence of absorption of blood or strong scattering in the deep parts of a living body and tumor tissue.

Considering this situation, a technique for obtaining internal information of a living body other than using optical CT and OCT has been disclosed in Japanese Patent Laid-open Publication No. 2000-88743. In this technique, ultrasound waves and light are radiated into a target portion inside a living body in order to detect how much the light is modulated by the ultrasound wave in the target portion. Thereby, information on the target portion of the living body can be obtained.

Generally, when treating tumor tissue such as a cancer, a proper technique is selected depending on the condition of an observed portion including the tumor tissue and the degree of invasion in the portion. Therefore, when treating tumor tissue such as a cancer, it is necessary to recognize an area, where the boundary between the tumor tissue and normal tissue exists, located in the depth direction of the target portion, before a technique is selected.

However, according to the optical measurement apparatus disclosed in the Japanese Patent Laid-open Publication No. 2000-88743, an area where the boundary between tumor tissue and normal tissue exists cannot be defined when the condition for obtaining information on the living body is not suitable. Consequently, there is a problem that the surgeon is excessively burdened during a surgical operation on tumor tissue.

SUMMARY OF THE INVENTION

The present invention has been made in consideration of the foregoing conventional situation, and an object of the present invention is to provide a biological observation apparatus and method which reduces the burden on the operator when treating tumor tissue.

A biological observation apparatus according to the present invention comprises: a sound wave radiating unit that radiates a sound wave into an object to be examined in living tissue; a light radiating unit that radiates light into the object; a light interfering unit that makes the light radiated from the light radiating unit Interfere with light reflected from an area where the sound wave reaches and radiates interference light; a light detector that detects the interference light radiated from the light interfering unit and outputs an interference signal corresponding to the interference light; and a calculation unit that calculates the amount of frequency modulation of the radiated light based on the interference signal outputted from the light detector and calculates a difference value between the two adjacent amounts of frequency modulation in sequence.

DETAILED DESCRIPTION OF THE PREFERRED EMBODIMENTS

Hereinafter, embodiments of the present invention will now be described in connection with the accompanying drawings.

Referring to FIGS. 1 to 9C, biological observation apparatuses according to embodiments of the present invention will now be described.

Figure 1:
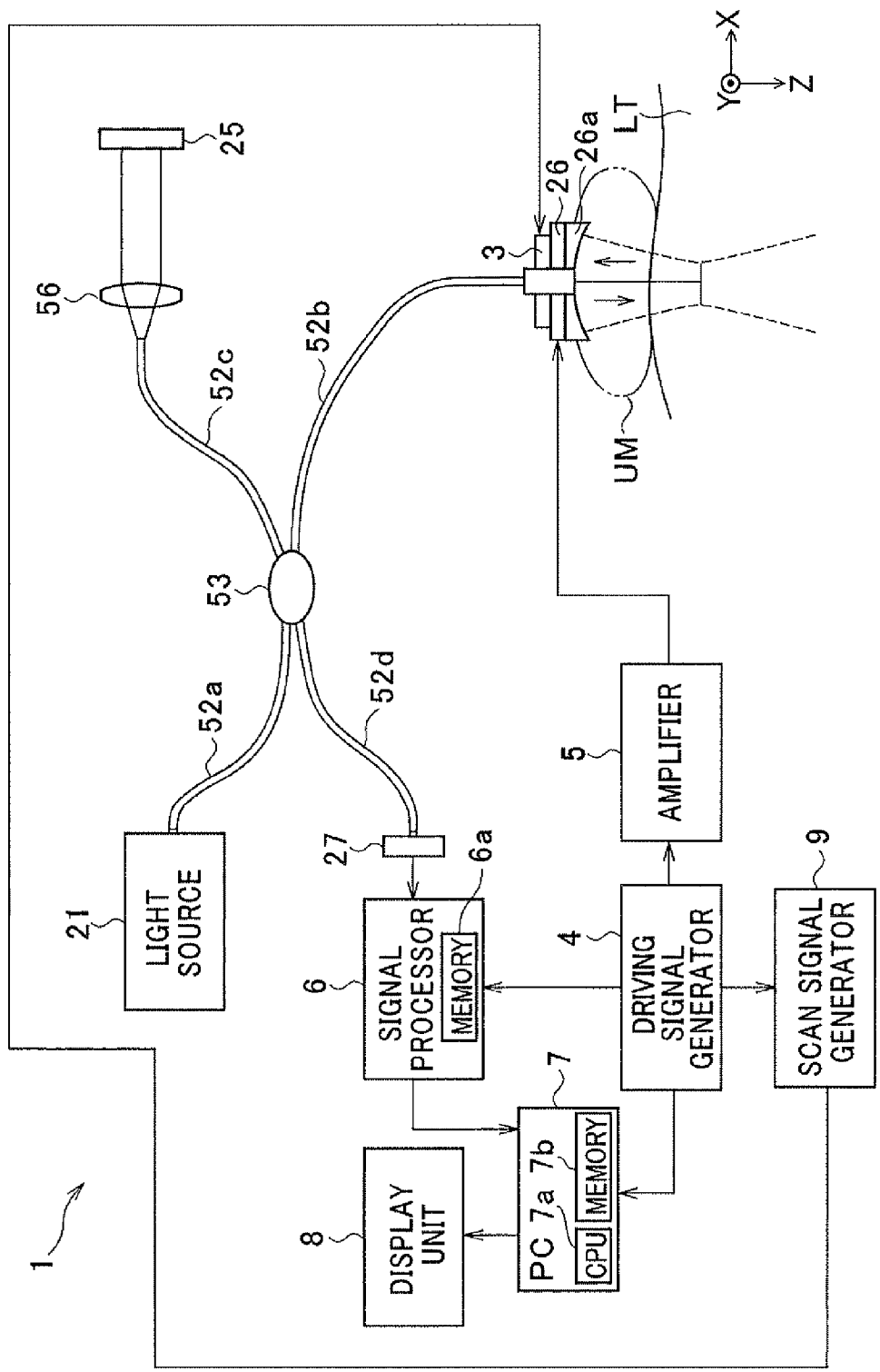
FIG. 1 is a block diagram exemplifying an outline of a biological observation apparatus according to an embodiment of the present invention.

FIG. 1 outlines a biological observation apparatus 1. This biological observation apparatus 1 comprises, as shown in FIG. 1, a scan unit 3, a driving signal generator 4, an amplifier 5, a signal processor 6, a personal computer (hereinafter, called "PC") 7, a display unit 8, a scan signal generator 9, a light source 21, a reference mirror 25, an ultrasound transducer 26 and an acoustic lens 26a with openings formed at their center, a light detector 27, optical fibers 52a, 52b, 52c, and 52d, an optical coupler 53, and a collimating lens 56, which are main parts.

Figure 2:
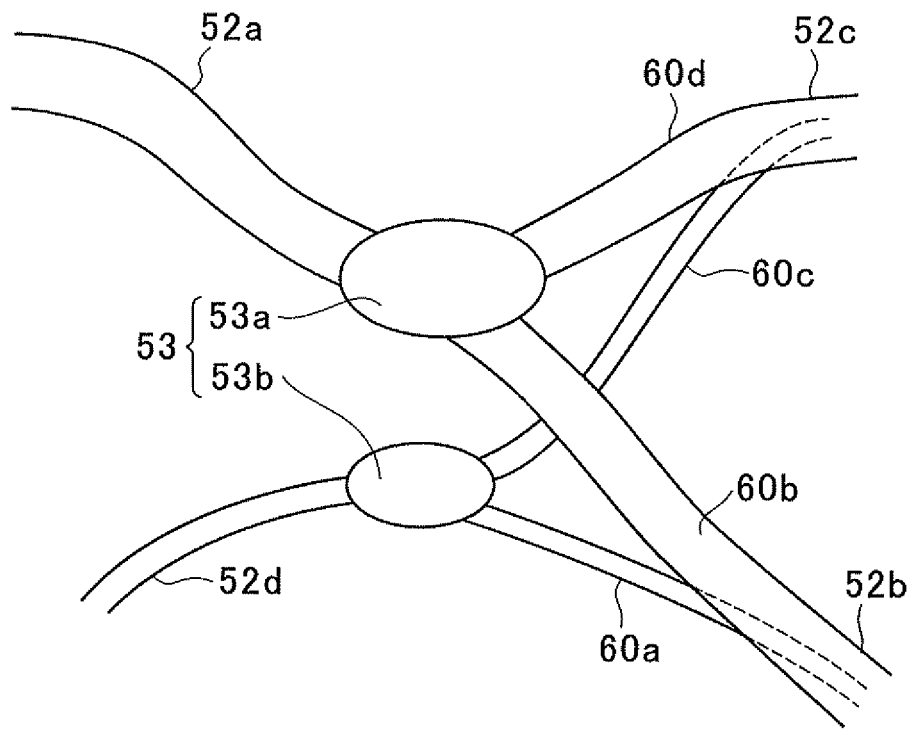
FIG. 2 is a diagram showing a configuration of an optical coupler in detail.

In addition, the optical coupler 53 comprises, as shown in FIG. 2, a first coupler 53a and a second coupler 53b.

Every time the scan unit 3 receives a scan signal outputted from the scan signal generator 9, the scan unit 3 changes the position (scan position) of the ultrasound transducer 26 with respect to living tissue LT in the X-axis or Y-axis direction shown in FIG. 1.

The driving signal generator 4 produces an ultrasound wave drive signal to make the ultrasound transducer 26 and the acoustic lens 26a radiate an ultrasound wave having a predetermined wavelength (or a predetermined frequency), and outputs the produced ultrasound wave drive signal to the amplifier 5. In addition, the driving signal generator 4 outputs a timing signal to the scan signal generator 9. The timing signal indicates the timing at which the ultrasound wave drive signal is outputted to the amplifier 5. Furthermore, when the scan position of the scan unit 3 reaches the end position of the scan range of the scan unit 3, the driving signal generator 4 outputs a trigger signal to the PC 7 and the scan signal generator 9.

The amplifier 5 comprises a power amplifier. This amplifier 5 amplifies the power of the ultrasound wave drive signal outputted from the driving signal generator 4, and provides the amplified ultrasound wave drive signal to the ultrasound transducer 26.

The scan signal generator 9 provides a scan signal for changing the scan position to the scan unit 3, based on the timing at which the scan signal generator 9 receives the timing signal and the trigger signal from the driving signal generator 4.

The light source 21 comprises a laser, which emits light which can enter into a target portion to be examined inside the living tissue LT, and a condenser lens, though not shown.

The optical fiber 52a has one end (first end) connected to the light source 21 and the other end (second end) connected to the first coupler 53a, as shown in FIGS. 1 and 2.

Figure 3:
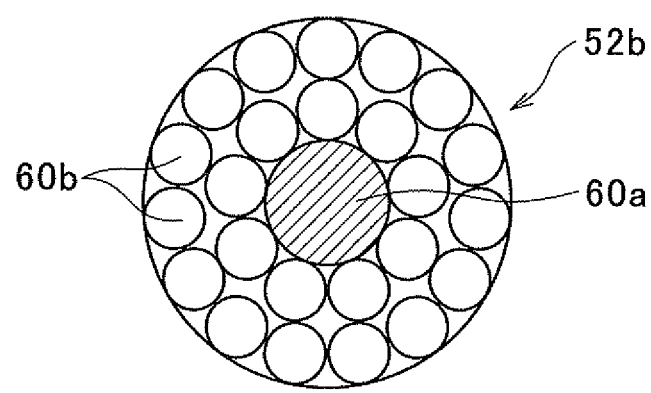
FIG. 3 is a sectional diagram exemplifying a configuration of an end part of an optical fiber.

The optical fiber 52b comprises, as shown in FIG. 2, a light-receiving fiber bundle 60a and a light-sending fiber bundle 60b. The fiber bundle 60a has one end (first end) connected to the second coupler 53b and the other end (second end) connected to the openings (not shown) formed at the center of the ultrasound transducer 26 and the acoustic lens 26a in such a manner that the other end (second end) is inserted therethrough. Meanwhile, the fiber bundle 60b has one end (first end) connected to the first coupler 53a and the other end (second end) connected to the openings formed at the center of the ultrasound transducer 26 and the acoustic lens 26a in such a manner that the other end (second end) is inserted therethrough. Both the other ends (second ends) of the fiber bundles 60a and 60b are arranged at the openings of the ultrasound transducer 26 and the acoustic lens 26a as illustrated in FIG. 3. In FIG. 3, the fiber bundle 60a is adapted to a core and surrounded by the fiber bundle 60b.

The ultrasound transducer 26 and the acoustic lens 26a radiate a predetermined ultrasound wave, which corresponds to the ultrasound wave drive signal received from the amplifier 5, in the direction in which light is radiated from the fiber bundle 60b arranged at the openings and toward the target portion inside the living tissue LT, while making the ultrasound wave converge. Thereby, the ultrasound wave radiated from the ultrasound transducer 26 and the acoustic lens 26a travels inside the living tissue LT as a cyclic compressional wave. The ultrasound wave converges at a predetermined area located in the depth direction (Z-axis direction shown in FIG. 1) of the living tissue LT.

Note that the acoustic lens 26a of the present embodiment can appropriately change the position, at which the ultrasound wave converges, in the depth direction (Z-axis direction shown in FIG. 1) of the living tissue LT under the control of, for example, the scan unit 3.

The optical fiber 52c comprises, as shown in FIG. 2, a light-receiving fiber bundle 60c and a light-sending fiber bundle 60d. The fiber bundle 60c has one end (first end) connected to the second coupler 53b and the other end (second end) arranged at a position where the light can come in from the collimating lens 56. Moreover, the fiber bundle 60d has one end (first end) connected to the first coupler 53a and the other end (second end) arranged at a position where the light can be radiated to the collimating lens 56.

The collimating lens 56 radiates the light coming from the fiber bundle 60d to the reference mirror 25 as parallel-flux light. In addition, the collimating lens 56 makes the light reflected from the reference mirror 25 converge so as to be radiated to the fiber bundle 60c.

The optical fiber 52d has, as shown in FIGS. 1 and 2, one end (first end) connected to the second coupler 53b and the other end (second end) connected to the light detector 27.

According to the configuration described above, the light emitted from the light source 21 is radiated to the living tissue LT via the optical fiber 52a, the first coupler 53a, and the fiber bundle 60b and to the collimating lens S6 via the optical fiber 52a, the first coupler S3a, and the fiber bundle 60d.

The light which enters the collimating lens 56 is converted to parallel-flux light and radiated to the reference mirror 25. This light is reflected from the reference mirror 25. The reflected light passes through the collimating lens 56 again, and enters the fiber bundle 60c as reference light. This reference light incident on the fiber bundle 60c is then radiated to the second coupler 53b.

Meanwhile, the light radiated into the living tissue LT via the fiber bundle 60b travels inside the living tissue LT in the depth direction (Z-axis direction shown in FIG. 1). The light reaches a portion corresponding to the area where the predetermined ultrasound wave radiated from the ultrasound transducer 26 and the acoustic lens 26a converges. The light is reflected from the portion. The light reflected from the portion enters the fiber bundle 60a as object light.

In the second coupler 53b, the object light coming from the fiber bundle 60a interferes with the reference light coming from the fiber bundle 60c, thereby producing interference light. The interference light enters the light detector 27 via the optical fiber 52d.

The light detector 27 applies heterodyne detection to the interference light coming from the second coupler 53b, and converts the detected interference light into an interference signal, which is an electric signal. The light detector 27 outputs the interference signal to the signal processor 6.

The signal processor 6 is provided with a memory 6a, and a spectrum analyzer or a digital oscilloscope (not shown).

The signal processor 6 detects the interference signal outputted from the light detector 27. At the first timing, the signal processor 6 calculates the Doppler shift amount (i.e., the amount of frequency modulation) of the light radiated from the light source 21 based on the detected interference signal. The signal processor 6 writes the Doppler shift amount into the memory 6a.

Next, at the second timing following the first timing, the signal processor 6 calculates Doppler shift amount in the same manner as at the first timing. The signal processor 6 calculates a difference value (a variation of Doppler shift amount) between the Doppler shift amount calculated at the first timing and written into the memory 6a and the Doppler shift amount calculated at the second timing. The signal processor 6 outputs the difference value to the PC 7. At the same time, the signal processor 6 overwrites the data in the memory 6a with the Doppler shift amount calculated at the second timing, thereby updating the data in the memory 6a. Subsequently, the signal processor 6 sets the second timing to the current (present, updated) first timing. The signal processor 6 calculates a difference value (a variation of Doppler shift amount) between the Doppler shift amount calculated at the current first timing and the Doppler shift amount calculated at the current second timing. The signal processor 6 outputs the difference value to the PC 7, and updates the data in the memory 6a in the same manner as described above. The signal processor 6 repeats the above process.

The PC 7 comprises a CPU (central processing unit) 7a, which performs various types of calculation and processing, and a memory 7b.

The CPU 7a relates the variations of Doppler shift amount sequentially outputted from the signal processor 6 to scan positional information which shows positions within a scan range of the living tissue LT where the scan can be performed by the scan unit 3. The variations of Doppler shift amount and the scan positional information, which are related to each other, are stored in the memory 7b.

Then, when the CPU 7a detects a state in which the scan is completed, based on a trigger signal outputted from the driving signal generator 4, the CPU 7a performs mapping to produce image data for one frame. The mapping is performed based on the variations of Doppler shift amount, which are stored in the memory 7b between the time when the previous trigger signal is inputted and the time when the current trigger signal is inputted, and the scan positional information which is related to the variations of Doppler shift amount. The CPU 7a converts the image data for one frame into a video signal and outputs the video signal to the display unit 8. Thereby, the display unit 8 displays an image (tomogram, tomographic image) of the inside of the living tissue LT in a plane such as an X-Z plane shown in FIG. 1.

Figure 4:
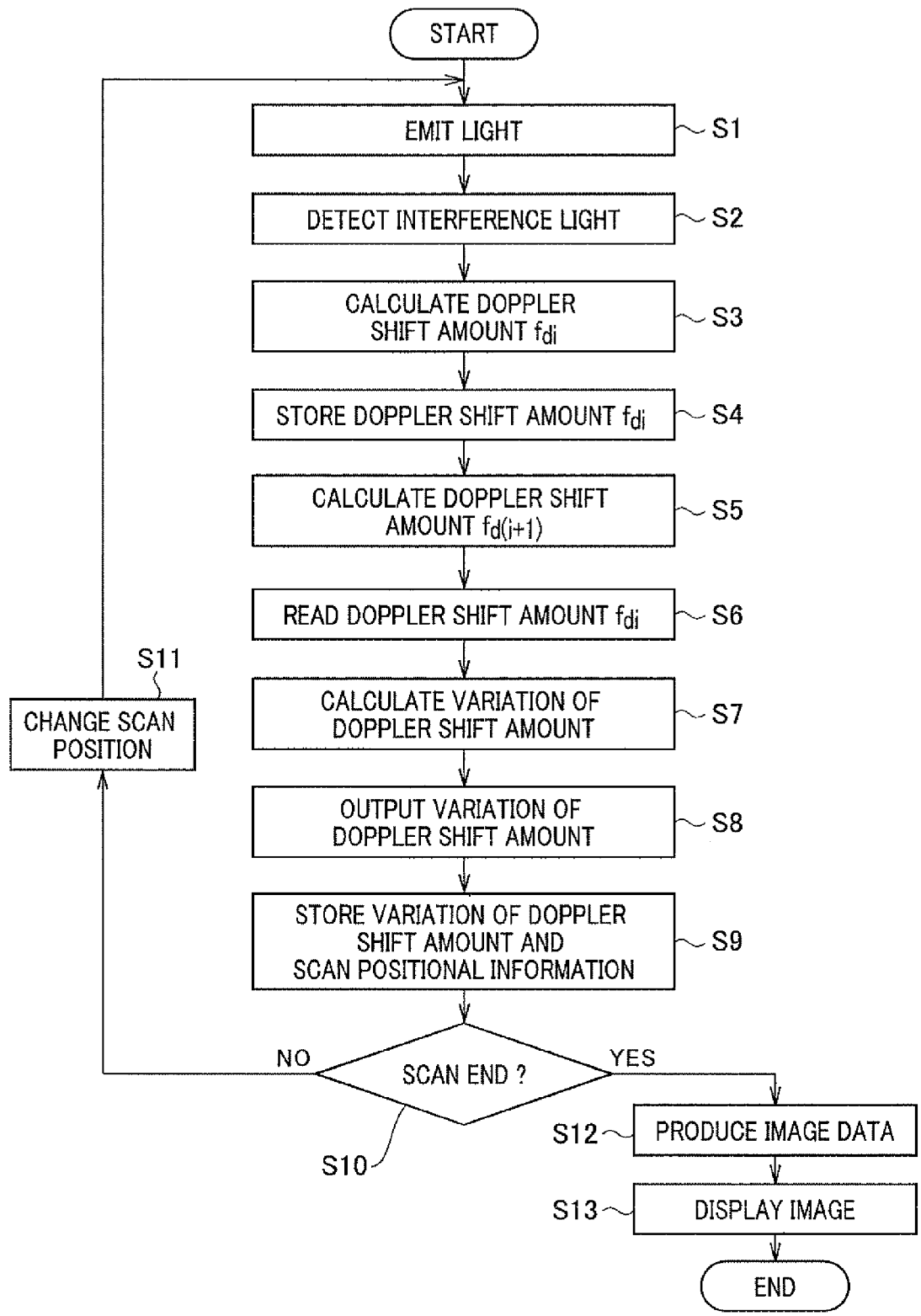
FIG. 4 is a flowchart showing operations of the biological observation apparatus.

Next, operations of the biological observation apparatus 1 according to the present embodiment will now be described with reference to a flowchart shown in FIG. 4.

First, an operator powers up each part of the biological observation apparatus 1, and positions the ultrasound transducer 26 (and the acoustic lens 26a) such that ultrasound waves and light are radiated in the Z-axis direction shown in FIG. 1 (i.e., the depth direction of the living tissue LT). Concurrently, a space between the ultrasound transducer 26 (and the acoustic lens 26a) and the living tissue LT is filled with an ultrasound transmissive medium UM, for example, water.

The operator then turns on switches, which are mounted in an operation device (not shown), to instruct to start obtaining biological information of the living tissue LT.

In step S1, the light source 21 emits light to the optical fiber 52a in response to the instruction from the operation device.

The light having a frequency of $f_L$ emitted from the light source 21 passes through the optical fiber 52a, the first coupler 53a, and the fiber bundle 60b and is radiated through the end of the fiber bundle 60b in the Z-axis direction (the depth direction in the living tissue LT) shown in FIG. 1.

The driving signal generator 4 outputs an ultrasound wave drive signal for radiating a predetermined ultrasound wave to the ultrasound transducer 26 via the amplifier 5 in response to the instruction from the operation device.

The ultrasound transducer 26 and the acoustic lens 26a radiate the predetermined ultrasound wave toward the living tissue LT in response to the inputted ultrasound wave drive signal. The ultrasound wave is radiated in the direction in which the light is radiated from the end of the fiber bundle 60b. The ultrasound wave radiated from the ultrasound transducer 26 and the acoustic lens 26a travels inside the living tissue LT as a cyclic compressional wave. The ultrasound wave converges at a predetermined area located in the depth direction (Z-axis direction shown in FIG. 1) of the living tissue LT.

The light radiated into the living tissue LT is reflected from the portion corresponding to the area where the ultrasound wave converges. The light reflected from the portion enters the fiber bundle 60a as object light.

In the second coupler 53b, the object light coming from the fiber bundle 60a interferes with the reference light coming from the fiber bundle 60c, thereby producing interference light in which a component of frequency $f_L$ is subtracted. The interference light is radiated to the light detector 27 via the optical fiber 52d.

In step S2, the light detector 27 applies heterodyne detection to the interference light coming from the second coupler 53b, and converts the detected interference light into an interference signal, which is an electric signal. The light detector 27 outputs the interference signal to the signal processor 6.

In step S3, the signal processor 6 detects the interference signal outputted from the light detector 27. The signal processor 6 calculates the Doppler shift amount (i.e., the amount of frequency modulation) $f_{di}$ of area $A_i$ (i=1, 2, ..., n, n+1, ...) based on the interference signal. The area $A_i$ includes an i-th portion located in the depth direction of the living tissue LT. The "i" is incremented by one for each portion sequentially located further from the surface layer of the living tissue LT to the inside of the living tissue LT. The i-th portion reflects the light. In step S4, the signal processor 6 writes the Doppler shift amount $f_{di}$ into the memory 6a.

In step S5, the signal processor 6 detects the interference signal outputted from the light detector 27. The signal processor 6 calculates the Doppler shift amount $f_{d(i+1)}$ of area $A_{i+1}$ (i=1, 2, ..., n, n+1, ...) based on the interference signal. The area $A_{i+1}$ includes an (i+1)-th portion located in the depth direction of the living tissue LT. The (i+1)-th portion reflects the light. In step S6, the signal processor 6 reads from the memory 6a the Doppler shift amount $f_{di}$ of the area $A_i$ including the i-th portion located in the depth direction of the living tissue LT. In step S7, the signal processor 6 calculates a difference value $(f_{di}-f_{d(i+1)})$ between the Doppler shift amount $f_{di}$ and the Doppler shift amount $f_{d(i+1)}$ as a variation of Doppler shift amount. In step S8, the signal processor 6 outputs the variation of Doppler shift amount to the PC 7. At the same time, the signal processor 6 overwrites the data in the memory 6a with the Doppler shift amount $f_{d(i+1)}$ of the area $A_{i+1}$, thereby updating the data in the memory 6a.

Meanwhile, it is generally known that the index of refraction of light varies between tumor tissue and normal tissue. Since the variation of the index of refraction relates to the variation of Doppler shift amount, a difference value between Doppler shift amounts of two areas in the tumor tissue is approximately zero, and a difference value between Doppler shift amounts of two areas in the normal tissue is also approximately zero. However, a difference value between a Doppler shift amount of an area in the tumor tissue and a Doppler shift amount of an area in the normal tissue is far from zero. That is, the Doppler shift amount of an area in the tumor tissue is significantly different from the Doppler shift amount of an area in the normal tissue.

Figure 5:
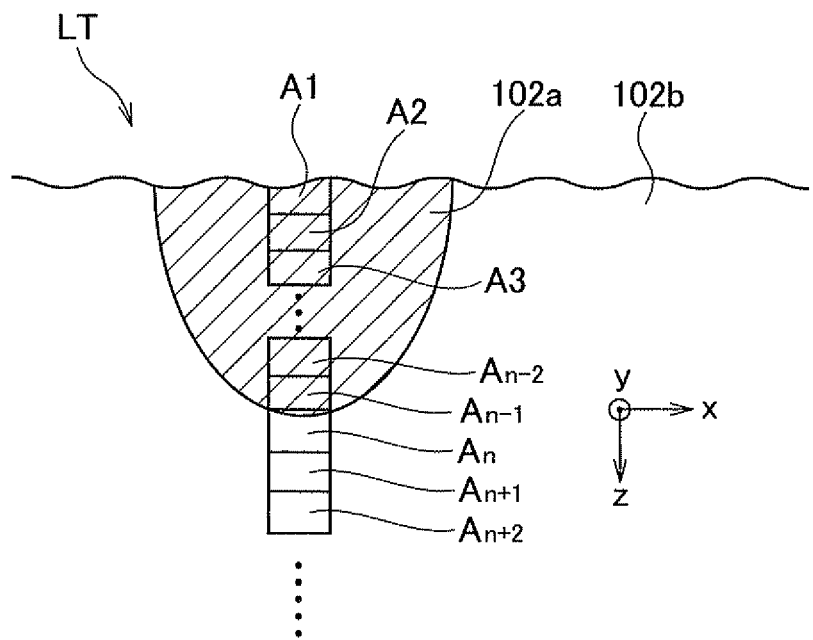
FIG. 5 is a sectional diagram exemplifying a state of tumor tissue existing in living tissue.

FIG. 5 is a sectional diagram exemplifying a state of tumor tissue existing in the living tissue LT. In FIG. 5, tumor tissue 102a and normal tissue 102b exist in the living tissue LT. In FIG. 5, $A_1$-$A_{n-1}$ show areas in the tumor tissue 102a, and $A_n$-$A_{n+2}$ ... show areas in the normal tissue 102b. Note that Doppler shift amounts of the areas $A_1$-$A_n$-$A_{n+2}$ ... are expressed as $f_{d1}$-$f_{dn}$-$f_{d(n+2)}$ ..., respectively. In this case, the variations of Doppler shift amount expressed as $(f_{d1}-f_{d2})$, $(f_{d2}-f_{d3})$, ..., $(f_{d(n-2)}-f_{d(n-1)})$ are approximately zero. The variations of Doppler shift amount expressed as $(f_{dn}-f_{d(n+1)})$, $(f_{d(n+1)}-f_{d(n+2)})$, ... are also approximately zero. The variation of Doppler shift amount expressed as $(f_{d(n-1)}-f_{dn})$ is a maximized value, which is far from zero.

That is, the signal processor 6 according to the present embodiment can obtain Information regarding an area in which the boundary between the tumor tissue 102a and the normal tissue 102b exists. The information corresponds to a value of a variation of Doppler shift amount of the specific area, which is significant compared with that of other areas.

In step S9, the CPU 7a of the PC7 relates values of $(f_{d1}-f_{d2})$, $(f_{d2}-f_{d3})$, ..., which are variations of Doppler shift amount, to scan positional information, which shows positions within a scan range where the scan can be performed by the scan unit 3. The CPU 7a stores the variations of Doppler shift amount and the scan positional information in the memory 7b.

In step S10, when the CPU 7a has not received a trigger signal from the driving signal generator 4, the CPU 7a detects a state in which the current scan position is not the end position of the scan range of the scan unit 3. In this case, in step S11, the CPU 7a controls the scan signal generator 9 to change the scan position in the X-axis or Y-axis direction shown in FIG. 1. After the scan position is changed, the above described operations from steps S1 to S9 are performed.

Figure 6:
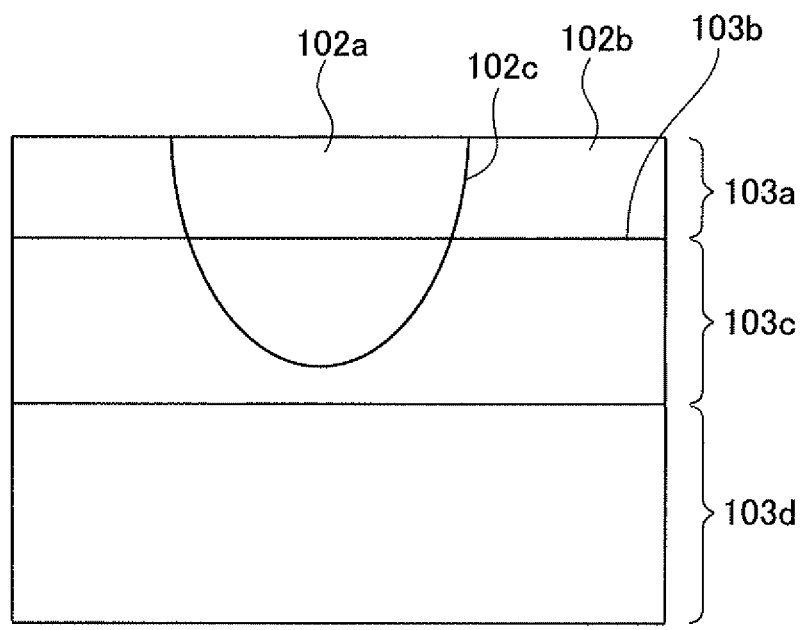
FIG. 6 is a diagram exemplifying a tomogram in which an area including the tumor tissue shown in FIG. 5 is visualized.

In step S10, when the CPU 7a has received a trigger signal from the driving signal generator 4, the CPU 7a detects a state in which the current scan position is the end position of the scan range of the scan unit 3 and the scan is completed. In step S12, the CPU 7a performs mapping to produce image data for one frame. The mapping is performed based on variations of Doppler shift amount, which are stored in the memory 7b between the time when the previous trigger signal is inputted and the time when the current trigger signal is inputted, and scan positional information related to the variations of Doppler shift amount. In step S13, the CPU 7a converts the image data for one frame into a video signal and outputs the video signal to the display unit 8. Thereby, as shown in FIG. 6, the display unit 8 displays an image (tomogram) of the target portion to be examined inside the living tissue LT in a plane such as an X-Z plane shown in FIGS. 1 and 5. In FIG. 6, the display unit 8 displays an area 102c (a boundary line) corresponding to the boundary between the tumor tissue 102a and the normal tissue 102b and a layer structure including a mucosal layer 103a, a muscle plate 103b, a submucosal layer 103c, and a muscle layer 103d, such that the area 102c is displayed as clear as the others.

Note that the image shown in FIG. 6, which is generated depending on variations of Doppler shift amount, may be displayed in a state where the image is superposed on an ultrasound wave tomogram which is obtained from the same portion where the image is obtained. In this case, the image of the layer structure of the living tissue including the mucosal layer 103a, the muscle plate 103b, the submucosal layer 103c, and the muscle layer 103d can be displayed more clearly.

As described above, since the biological observation apparatus 1 according to the present embodiment can define the portion invaded by tumor tissue inside living tissue, an operator can easily select a technique for treating the tumor tissue. Consequently, the biological observation apparatus 1 can reduce the burden on an operator when treating tumor tissue.

The above-described method for generating an image depending on variations of Doppler shift amount is not limited to the biological observation apparatus 1 in which Doppler shift amounts of portions located in the depth direction of the living tissue LT are individually obtained. The method can be used in a biological observation apparatus 1A shown in FIG. 7 which can obtain Doppler shift amounts of plural portions located in the depth direction of the living tissue LT at one time.

Figure 7:
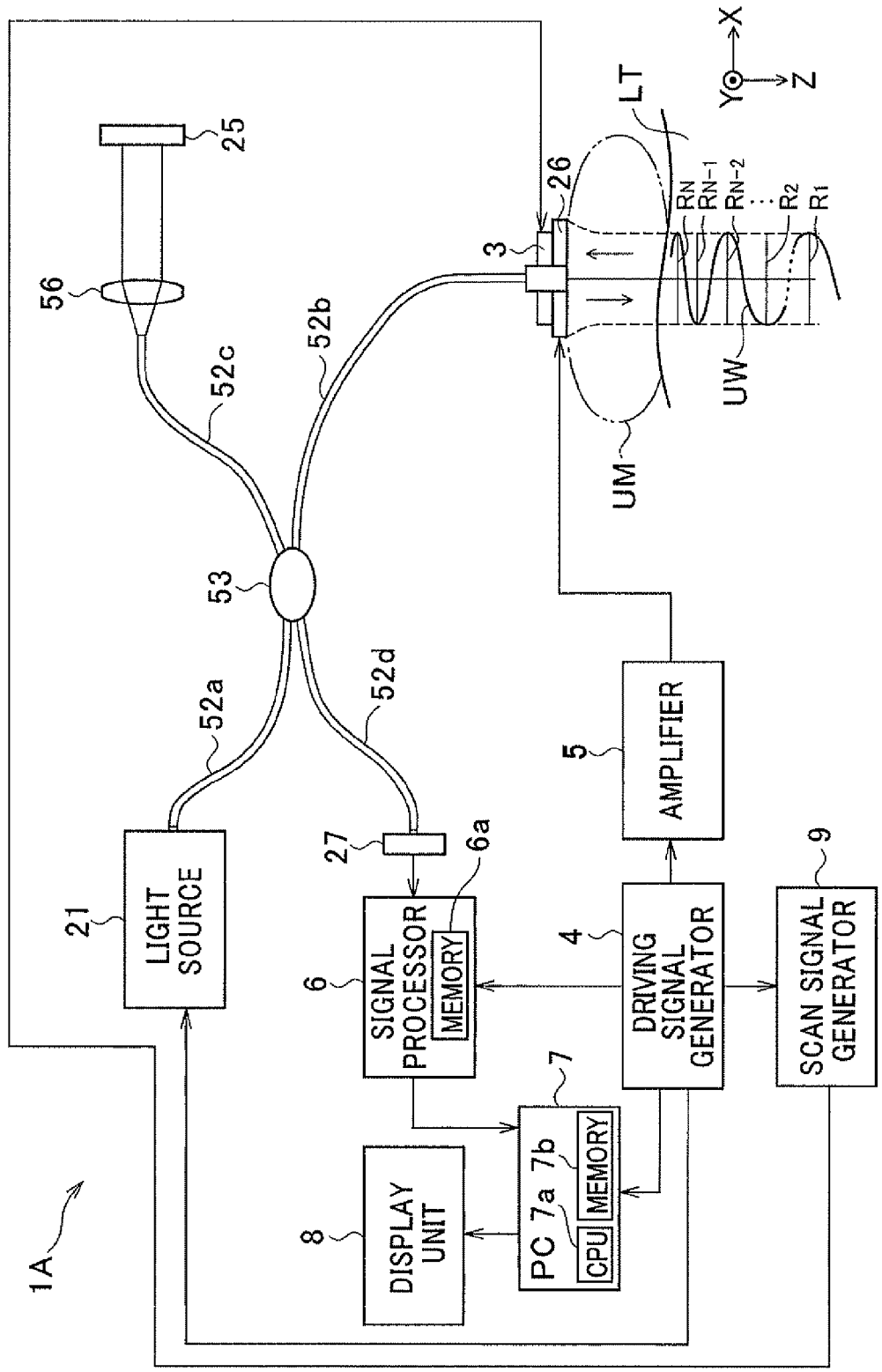
FIG. 7 is a block diagram exemplifying an outline of a biological observation apparatus according to another embodiment of the present invention.

The biological observation apparatus 1A comprises, as shown in FIG. 7, the scan unit 3, the driving signal generator 4, the amplifier 5, the signal processor 6, the PC 7, the display unit 8, the scan signal generator 9, the light source 21, the reference mirror 25, the ultrasound transducer 26, the light detector 27, the optical fibers 52a, 52b, 52c, and 52d, the optical coupler 53, and the collimating lens 56, which are main parts.

Figure 8:
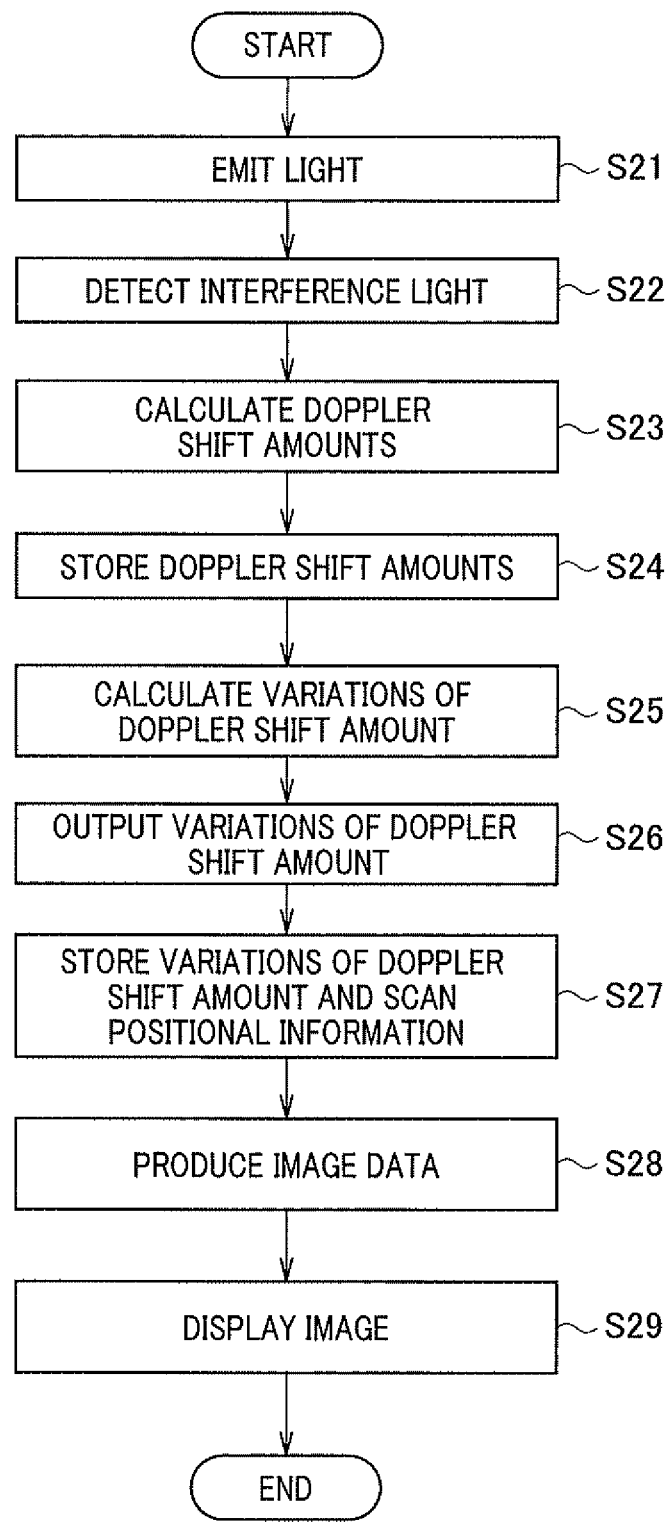
FIG. 8 is a flowchart showing operations of the biological observation apparatus.

Next, operations of the biological observation apparatus 1A will now be described with reference to a flowchart shown in FIG. 8. Note that, hereinafter, descriptions of the same operations of the biological observation apparatus 1A as those of the biological observation apparatus 1 are appropriately omitted.

First, an operator powers up each part of the biological observation apparatus 1A, and positions the ultrasound transducer 26 such that ultrasound waves and light are radiated in the Z-axis direction shown in FIG. 7 (i.e., the depth direction of the living tissue LT). Concurrently, a space between the ultrasound transducer 26 and the living tissue LT is filled with the ultrasound transmissive medium UM, for example, water.

The operator then turns on switches, which are mounted in the operation device (not shown), to instruct to start obtaining biological information of the living tissue LT.

Figure 9A:
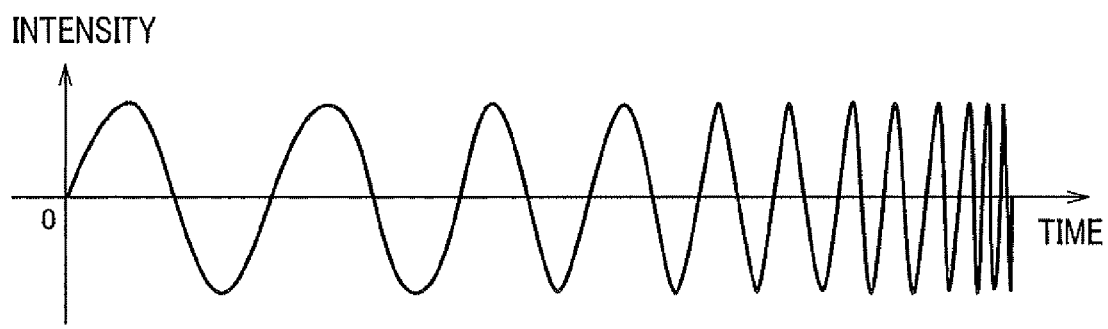
FIG. 9A exemplifies a waveform of an ultrasound wave radiated to living tissue by the biological observation apparatus shown in FIG. 7.
Figure 9B:
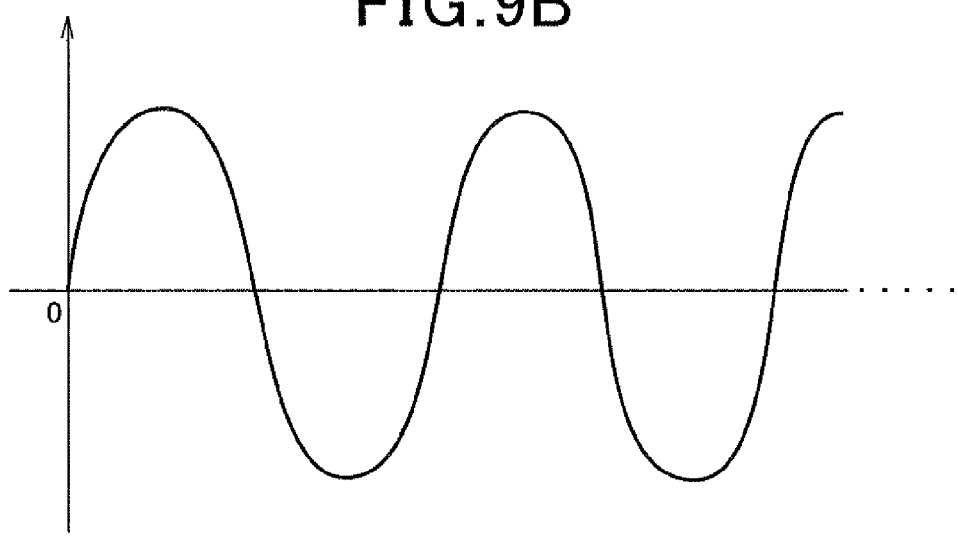
FIG. 9B details a start part of the waveform shown in FIG. 9A.

In response to the instruction from the operation device, the driving signal generator 4 outputs an ultrasound wave drive signal to the ultrasound transducer 26 via the amplifier 5, where the ultrasound wave drive signal is for radiating ultrasound waves having a waveform, for example, shown in FIG. 9A toward the living tissue LT. FIG. 9B details a beginning part of the waveform shown in FIG. 9A, while FIG. 9C details an end part of the waveform shown in FIG. 9A.

Figure 9C:
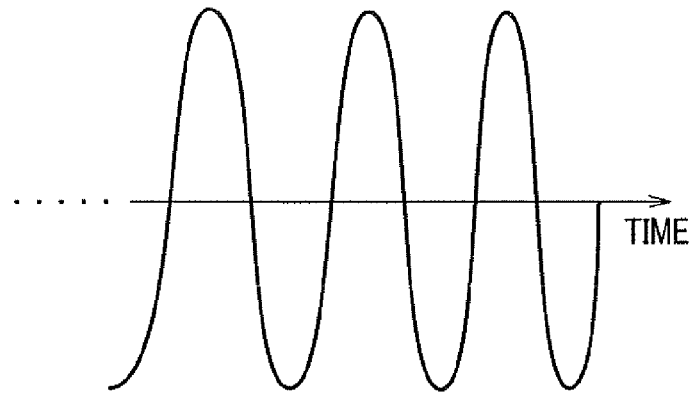
FIG. 9C details an end part of the waveform shown in FIG. 9A.

Practically, as shown in FIGS. 9A to 9C, the ultrasound wave has frequencies which become higher as time elapses (that is, each period becomes shorter) and has intensities which are maximized at different timings at one scan position.

Accordingly, the ultrasound wave having the waveform shown in FIG. 9A is radiated from the ultrasound transducer 26 and travels inside the living tissue LT as a cyclic compressional wave whose frequency successively changes. Subsequently, the densities of the living tissue LT are maximized at each of positions (portions) in the depth direction (Z-axis direction shown in FIG. 7) in the living tissue LT. The positions correspond to the timings at which the intensities of the ultrasound wave are maximized. That is, the ultrasound wave radiated from the ultrasound transducer 26 travels inside the living tissue LT in its depth direction as a longitudinal compressional wave from its lower-frequency wave parts (i.e., longer wavelengths) in sequence. Hence, the frequencies of the ultrasound wave entering the living tissue become higher over time (i.e., the wavelengths become shorter). Note that the ultrasound wave radiated from the ultrasound transducer 26 may be a pulsed wave, and not limited to a continuous wave.

The ultrasound wave radiated from the ultrasound transducer 26 and traveling inside the living tissue LT applies pressure to the living tissue LT depending on its degrees of compression, which will give local compression to the tissue so that the tissue density is locally changed. This results in that, as indicated by UW in FIG. 7, the densities of the living tissue LT are maximized at each of Z-axis directional (depth directional) positions (portions) in the living tissue LT, where the intensities of the ultrasound wave are maximized.

Those locally compressed tissue portions are greater in density than the other portions, so that such locally density-maximized tissue portions are able to strongly reflect (and scatter) light. In FIG. 7, these local density-maximized tissue portions located in the Z-axis direction inside the living tissue LT are shown as wave fronts $R_1, R_2, \ldots, R_N$ of the ultrasound wave. At a time instant when the radiation of the ultrasound wave has just been completed, the ultrasound wave fronts $R_1, R_2, \ldots, R_N$ are spatially located along the transmission direction of the ultrasound wave (Z-axis direction) in sequence.

The driving signal generator 4 outputs a timing signal, which indicates the timing at which the ultrasound wave drive signal is outputted at one scan position, to the light source 21.

In step S21, the light source 21 emits light to the optical fiber 52a immediately after inputting the timing signal.

The light having a frequency of $f_L$ emitted from the light source 21 passes through the optical fiber 52a, the first coupler 53a, and the fiber bundle 60b and is radiated through the end of the fiber bundle 60b in the Z-axis direction (the depth direction in the living tissue LT) shown in FIG. 7.

The light radiated from the end of the fiber bundle 60b is reflected from the portions inside the living tissue LT where the densities are maximized by the ultrasound wave having the waveform shown in FIG. 9A, and enters the fiber bundle 60a as object light.

In the second coupler 53b, the object light coming from the fiber bundle 60a interferes with the reference light coming from the fiber bundle 60c, thereby producing interference light in which a component of frequency $f_L$ is subtracted. The interference light is radiated to the light detector 27 via the optical fiber 52d.

In step S22, the light detector 27 applies heterodyne detection to the interference light coming from the second coupler 53b, and converts the detected interference light into an interference signal, so which is an electric signal. The light detector 27 outputs the interference signal to the signal processor 6.

In step S23, the signal processor 6 calculates Doppler shift amounts (i.e., the amount of frequency modulation) $f_{d1}, f_{d2}, \ldots, f_{d(n-1)}, f_{dn}, \ldots$ of areas $A_1, A_2, \ldots, A_{d(n-1)}, A_n, \ldots$ which include positions reflecting the light inside the living tissue LT, based on the interference signal outputted from the light detector 27 and the timing at which the timing signal is received. In step S24, the signal processor 6 stores calculated Doppler shift amounts in the memory 6a. In step S25, the signal processor 6 sequentially calculates variations of Doppler shift amount shown by $(f_{d1}-f_{d2}), (f_{d2}-f_{d3}), \ldots, (f_{d(n-1)}-f_{dn}), \ldots$ and, in step S26, outputs the variations to the PC 7.

In step S27, the CPU 7a of the PC7 relates values of $(f_{d1}-f_{d2}), (f_{d2}-f_{d3}), \ldots$, which are variations of Doppler shift amount, to scan positional information, which shows positions within a scan range where the scan can be performed by the scan unit 3. The CPU 7a stores the variations of Doppler shift amount and the scan positional information in the memory 7b.

In step S28, when the CPU 7a has received a trigger signal from the driving signal generator 4, the CPU 7a detects a state in which the scan is completed. The CPU 7a performs mapping to produce image data for one frame. The mapping is performed based on the variations of Doppler shift amount, which are stored in the memory 7b between the time when the previous trigger signal is inputted and the time when the current trigger signal is inputted, and the scan positional information related to the variations of Doppler shift amount. In step S29. The CPU 7a converts the image data for one frame into a video signal and outputs the video signal to the display unit 8. Thereby, as shown in FIG. 6, the display unit 8 displays an image (tomogram) of the target portion to be examined inside the living tissue LT in a plane such as an X-Z plane shown in FIGS. 5 and 7.

As described above, the biological observation apparatus 1A according to another embodiment can provide the same advantages as those of the biological observation apparatus 1.

According to the biological observation apparatus and method of the embodiments of the present invention, the burden on an operator can be reduced when treating tumor tissue.

Although the description above contains many specificities, these should not be construed as limiting the scope of the invention but as merely providing illustrations of some of the presently preferred embodiments of the present invention. Thus the scope of the present invention should be determined by the appended claims.

What is claimed is:

1. A biological observation apparatus comprising:
   a sound wave radiating unit configured to radiate an ultrasound wave into an object to be examined, the object located in living tissue, wherein the sound wave radiating unit radiates the ultrasound wave as a cyclic compressional wave while successively changing a frequency of the ultrasound wave to increase the density of a portion of the object to be examined in the living tissue;
   a light radiating unit configured to radiate light into the object;
   a light interfering unit configured to generate interference light by causing the light radiated from the light radiating unit to interfere with light reflected from the portion of the object with the increased density, and further configured to radiate said interference light;
   a light detector configured to detect the interference light radiated from the light interfering unit and outputs an interference signal corresponding to the interference light;
   a memory unit configured to store interference signals; and
   a calculator configured to calculate an amount of frequency modulation of the radiated light based on the interference signals, which are outputted from the light detector and correspond to individual timings sequentially outputted from the memory unit, and sequentially calculates a difference value between the amounts of frequency modulation of two observed areas that are adjacent to each other in a depth direction in the living tissue, wherein the calculator is further configured to relate the difference value to a position with respect to the living tissue, stores the difference value and the position, and generates a tomographic image of the object based on the difference value and the position.

2. The apparatus according to claim 1, wherein the calculation unit is further configured to store a first amount of frequency modulation calculated at a first timing and calculates the difference value between the first amount of frequency modulation and a second amount of frequency modulation calculated at a second timing.

3. The apparatus according to claim 2, wherein the calculation unit is further configured to overwrite the stored a first amount of frequency modulation with the second amount of frequency modulation and sets the second timing to current first timing.

4. The apparatus according to claim 1, wherein the calculation unit is further configured to store the calculated amounts of frequency modulation.

5. The apparatus according to claim 1, further comprising a sound wave converging unit configured to radiate the ultrasound wave into the object while making the ultrasound wave converge.

6. The apparatus according to claim 1, further comprising a scan unit configured to change a position of the sound wave radiating unit and the light radiating unit with respect to the living tissue.

7. The apparatus according to claim 1, wherein the calculation unit is further configured to produce image data of the living tissue based on the difference value and the position with respect to the living tissue.

8. The apparatus according to claim 7, further comprising a display unit configured to display an image of the living tissue based on the image data.

9. The apparatus according to claim 1, wherein the sound wave radiating unit is positionable so that the ultrasound wave and the light are radiated in the same depth direction in the living tissue.

10. A biological observation method comprising:
radiating an ultrasound wave into an object to be examined, the object located in living tissue, wherein the ultrasound wave is radiated as a cyclic compressional wave while successively changing a frequency thereof to increase the density of a portion of the object to be examined in the living tissue;

radiating light into the object;

generating interference light by causing the light radiated from the light radiating unit to interfere with light reflected from the portion of the object with the increased density, and further radiating said interference light;

detecting the radiated interference light;

outputting an interference signal corresponding to the interference light;

calculating the amounts of frequency modulation of the radiated light based on the outputted interference signals, which correspond to individual timings sequentially outputted from the memory unit;

sequentially calculating a difference value between the amounts of frequency modulation of two observed areas that are adjacent to each other in a depth direction in the living tissue;

relating the difference value to a position with respect to the living tissue;

storing the difference value and the position; and generating a tomographic image of the object based on the difference value and the position.

11. The method according to claim 10, wherein the ultrasound wave is radiated as a converging wave into the object.

12. The method according to claim 10, wherein the ultrasound wave and light are radiated in the same depth direction in the living tissue.

* * * * *